United States Patent [19]

Shealy et al.

[11] Patent Number: 4,564,509
[45] Date of Patent: Jan. 14, 1986

[54] METHOD AND APPARATUS FOR IMPROVED GETTERING FOR REACTANT GASES

[75] Inventors: James R. Shealy; Lester F. Eastman, both of Ithaca, N.Y.

[73] Assignee: Northeast Semiconductor Inc., Ithaca, N.Y.

[21] Appl. No.: 509,871

[22] Filed: Jun. 30, 1983

[51] Int. Cl.[4] .............................................. B01D 47/02
[52] U.S. Cl. ................................ 423/210.5; 423/624; 423/219
[58] Field of Search ...................... 423/219, 210.5, 624, 423/625

[56] References Cited

U.S. PATENT DOCUMENTS 1,050,902  1/1913  Acker .................................. 423/210.5
2,421,568  6/1947  Kurland .............................. 423/219

FOREIGN PATENT DOCUMENTS 0153321  11/1950  Australia ........................... 423/210.5
1544145   6/1972  Fed. Rep. of Germany ...... 423/219

OTHER PUBLICATIONS

Shealy et al., "A New Technique for Gettering Oxygen and Moisture from Gases Used in Semiconductor Processing", *Appl. Phys. Lett.* 41(1), 1/7/82.
Hansen, "*Constitution of Binary Alloys*", 12/58, p. 145.
Tsai et al.; "Characterization of $Al_{0.06}Ga_{0.94}As$ Grown by OMVPE for Low Current/High Efficiency Light Emitting Diodes", *Int. Phys. Conf.*, 12/82.
Shealy et al.; "Improved Photoluminescence of Organometallic Vapor Phase Epitaxial AlGaAs Using a New Gettering Technique on an Arsine Source", *App. Phys. Lett.*, vol. 42, 1/1/83.
Marinace, *IBM Technical Disclosure Bulletin*, vol. 15, No. 7, 12/72, "Room Temperature Scrubber".

*Primary Examiner*—L. Dewayne Rutledge
*Assistant Examiner*—S. Kastler
*Attorney, Agent, or Firm*—Barnard and Brown

[57] ABSTRACT

A method of removing oxygen and water vapor and other oxygen bearing gas species from reactant gases comprising the use of an appropriate solution containing an active gettering metal, selected from the group of aluminum, magnesium, calcium and lithium in liquid phase through a moderate temperature range, including room temperature and above as an oxygen gettering step, through the formation of an oxide of said metal wherein the said metal becomes continuously available for oxidation by exposing the said unreacted metal to the gas by bubbling the reactant gas through a ternary melt of gallium-indium and the said metal in a nonreactive container and maintaining in solid phase an excess of the active gettering method so that the capacity for removing the oxygen and water vapor and other oxygen bearing gas species may be extended by the active metal going into solution in the melt from the solid as the metal oxide is formed and goes out of solution.

17 Claims, 6 Drawing Figures

METHOD AND APPARATUS FOR IMPROVED GETTERING FOR REACTANT GASES

This invention relates to a novel method for gettering oxygen and moisture from reactant gas to minimize oxidation reactions when these gases are put to use. More particularly, this invention relates to the gettering of oxygen and water vapor and other oxygen bearing gas species from the reactant gases used in the process in the fields of epitaxial semiconductor growth and/or processing, vapor or plasma etching or thin film disposition or any other field wherein the presence of oxygen and water vapor and other oxygen bearing gas species, in combination with a reactant gas must be controlled to a high degree of purity.

Many publications depict the problems of the presence of oxygen and water vapor in combination with reactant gases. They include:

(1) Paper entitled "Characterization of A10.06 Ga0.94 As grown by OMVPE for low current/high efficiency light emitting diodes" by M. J. Tsai, M. M. Tashima, B. L. Twu and R. L. Moon, International Physical Conference Ser. No. 65 © 1983; Chapter 2 (Paper presented at International Symp. GaAs and Related Compounds, Albuquerque, 1982, and;

(2) article authored by J. R. Shealy, V. G. Kreismanis, D. K. Wagner and J. M. Woodall, entitled "Improved photoluminescence of organometallic vapor phase epitaxial AlGaAs using a new gettering technique on the arsine source" and published in Appl. Phys. Lett. Vol. 42 No. 1, Jan. 1, 1983.

Other publications which are pertinent to the invention described herein are the following:

(3) IBM Technical Disclosure Bulletin Vol. 15, No. 7, 1972 entitled "Room Temperature for Scrubber" by J. C. Marinace; and (4) An article by J. R. Shealy and J. M. Woodall entitled "A new technique for gettering oxygen and moisture from gases used in semiconductor processing" and published in Appl. Phys. Lett. 41(1), July 1, 1982 by the American Institute of Physics.

The IBM Technical Disclosure Bulletin article teaches the use of a eutectic alloy of gallium and indium as a room temperature liquid for removing oxygen and water from unspecified gases wherein the alloy has been heated to 100° C. and an excess of aluminum is added so that upon cooling to room temperature, a small amount of aluminum is dissolved in the eutectic alloy. The aluminum in the alloy serves as a gas scrubber. Although the amount of the aluminum dissolved in the eutectic is very small at room temperature, aparently it is effective as a scrubber. As the aluminum is used in the formation of $Al_2O_3$, more goes into solution. Apparently the amount of aluminum available to go into solution at room temperature as $Al_2O_3$ is formed is that amount which comes out of solution when the eutectic alloy is cooled from 100° C. to room temperature. For very high flow rates of gas or for larger proportions of $O_2$ in the gas, larger amounts of eutectic can be used, or it can be heated above room temperature. In any event, the availability of aluminum to go into solution is dependent on how much aluminum went into solution at the time the eutectic was heated to 100° C. and the amount which came out of solution on cooling the eutectic to room temperature. However effective, the eutectic alloy with aluminum in solution is as a scrubber of $O_2$ from a gas, it has limited effectiveness over time because of the limited availability of aluminum to go into solution and is at best a batch process for removing oxygen and water vapor from the gas being scrubbed.

The IBM Technical Bulletin further states that for very large flow rates of gas or for larger proportions of $O_2$ in the gas, larger amounts of eutectic can be used, or it can be heated above room temperature. Following the teachings of the Bulletin, the larger eutectic would give more aluminum to come out of the solution when the temperature was lowered from 100° C. and leaves more aluminum in the solution, but it would not necessarily increase the rate of the formation of $Al_2O_3$. The raising of the temperature of the eutectic toward 100° C. would not increase the total available aluminum in the solution or available to go into the solution and not necessarily increase the rate of the formation of $Al_2O_3$ to remove the oxygen in the gas. Moreover, any error in the attempt to operate the melt of gallium-indium sharply at the eutectic composition makes the melt subject to driving the gallium-indium into a two phase solution (liquid and solid) and makes the melt intolerant to relative minor decreases in the ambient temperature of the melt because of the steep slope on the indium rich side of the eutectic.

In any event, the publication of the IBM Technical Disclosure Bulletin in 1972 did not teach researchers, scientists, and technical people concerned with the problem how to reduce the oxygen and water in reactant gases with a high purity required by the fields of technology identified above.

On page one of the article referred to above, Appl. Phys. Lett. 41(1), July 1, 1982 by the American Institute of Physics, a summary of the techniques used by those skilled in the art to obtain purity in gases with respect to oxygen and water is reported as follows:

Standard techniques for the purification (removal of oxygen and water vapor) of process gases include (i) the catalytic conversion of oxygen to water vapor and subsequent removal of the water vapor using a molecular sieve, (ii) the use of a gettering furnace usually containing titanium for the removal of impurities from hydrogen. With the first method, the use of corrosive gases and the extent of contamination from sieve materials such as alumina silicates or activated charcoal is questionable. This second method using the titanium gettering furnace is not applicable for the purification of nitrogen and corrosive gases and its capacity for the removal of oxygen or water vapor is somewhat limited. Finally, the hot palladium diffusion cell is applicable to hydrogen only and is susceptible to damage (microcracks in the palladium) if allowed to cool with hydrogen present.

The aforesaid article in Applied Physic Letters of July 1, 1982 describes a method of purification of process gases using free aluminum as the primary gettering element in gallium-indium solution through an upward range of temperatures beginning at a lower room temperature to a temperature below where the gas being treated would thermally decompose. The process gas being gettered is bubbled through a two phase solution consisting of a ternary melt of gallium-indium saturated with aluminum and solid aluminum is added so that the solution can remain saturated with aluminum as the aluminum is consumed by oxidizing in the presence of process gas. This allows for a very high capacity for removal of oxygen and water vapor. The melt of gallium ad indium was on the gallium rich side of the eutectic and produced a liquid solution at room temperature (about 24° C.). The melt was saturated with aluminum at room temperature. The melt was contained in a bubbler made of quartz, a non-reactive material. The method reported in the Appl. Phys. Lett. Vol. 41 No. 1, July 1, 1982, is distinctively novel over the said IBM Technical Disclosure Bullentin because it is not a batch process, it used a bubbler technique. The saturation of the gallium-indium solution with aluminum is accomplished at room temperature rather than while it is heated to 100° C.; and rather than cooled to room temperature to provide excess aluminum. The bubbler allows the water vapor and oxygen in the reactant gas to diffuse to the edge of the bubble and come in contact with the aluminum in the solution to form the $Al_2O_3$. The method reported in the Appl. Phys. Lett. Vol. 41 No. 1, July 1, 1982 functioned to getter water vapor and oxygen from two relatively inert gases, $H_2$ and $N_2$ to a high degree of purity, i.e. 1,000 parts per million of moisture, reduced to less than 1 part per million. However, $H_2$ and $N_2$ are not normally reactant gases from which high purity from water vapor and oxygen is required in the fields of epitaxial semiconductor growth and/or processing, vapor or plasma etchings, plasma deposition, or thin film disposition, etc.

The article referred to above, Appl. Phys. Lett. 42(1), Jan. 1, 1983, reported the successful purification of water and oxygen from arsine gas to a high degree so that arsine (which is normally a major source of moisture) could be used in the growth of AlGaAs by organometallic vapor phase epitaxy (OMVPE), so that the material showed improved photoluminescence efficiency. This article illustrates some of the benefits of the invention to be described herein even though it does not describe the details of the method and apparatus to obtain the purified arsine.

Accordingly, it is an object of the present invention to provide a novel method and apparatus for gettering oxygen and/or water vapor and/or other oxygen bearing gas species from reactant gases used in the process in fields of epitaxial semiconductor growth and/or processing, vapor or plasma etching or thin film disposition or any other field wherein the presence of oxygen and/or water vapor and/or other oxygen bearing gas species in a reactant gas must be controlled to a high degree of accuracy.

It is still another object of the present invention to provide a method of and apparatus for removing oxygen and/or water vapor and/or other oxygen bearing gas species from reactant gases comprising the use of an appropriate solution containing an active gettering metal, selected from the group of aluminum, magnesium, calcium and lithium in liquid phase through a moderate temperature range, including room temperature and above as an oxygen gettering step, through the formation of an oxide of said metal wherein the said metal becomes continously available for oxidation by exposing the said unreacted metal to the gas by bubbling the reactant gas through a ternary melt of gallium-indium and the said metal in a nonreactive container.

It is still another object of the present invention to provide a method of and apparatus for removing oxygen and/or water vapor and/or other oxygen bearing gas species from reactant gases comprising the use of an appropriate solution containing an active gettering metal, selected from the group of aluminum, magnesium, calcium and lithium in liquid phase through a moderate temperature range, including room temperature and above as an oxygen gettering step, through the formation of an oxide of said metal wherein the said metal becomes continously available for oxidation by exposing the said unreacted metal to the gas by bubbling the reactant gas through a ternary melt of gallium-indium and the said metal in a nonreactive container and maintaining in solid phase an excess of the active metal so that the capacity for removing the oxygen and water vapor and other oxygen bearing gas species may be extended by the active metal continously going into solution on the melt from the solid as the metal oxide is formed and goes out of solution.

Still other objects of the present invention will be described hereinafter including all the embodiments, as well as the applicability of the invention to purifying a very wide range of reactant gases over a wide range of applications where the presence of oxygen, moisture and/or other oxygen bearing gas species are present in reactant gases and such is detrimental to the field of application.

Figure 5:
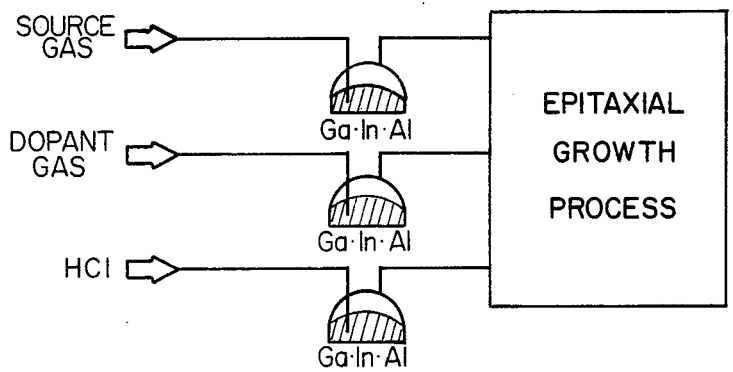

FIG. 5 is a diagramatic illustration of how the teachings of the present invention could be applied to the epitaxial growth process, the source gas, the dopant gas and the HCl could each be purified prior to use depending upon the need for the same in the epitaxial and the quality of the gas source with respect to oxygen, moisture and/or other oxygen bearing gas species included in the reactant gas.

Figure 6:
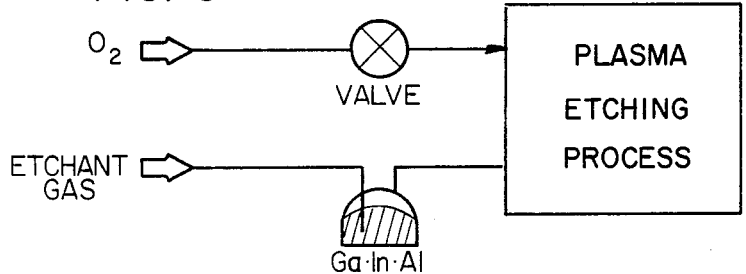

FIG. 6 is a diagramatic illustration of the teachings of the present invention could be used to improve the etchant gas in a plasma etching process when the etchant gas contains unwanted oxygen, moisture and/or other oxygen bearing gas species included in the reactant gas.

As stated in the publication Appl. Phys. Lett. 41(1), July 1, 1982, the purity of gases used in semiconductor processing is of prime importance in the majority of device fabrication schemes. Metallurgy on semiconductors involving materials which are highly reactive with oxygen such as aluminum and titanium [R. A. Swalin, Thermodynamics of Solids (Wiley, New York, 1972,) 2nd ed., pp. 104-118] requires ambients with very low levels of oxygen and water vapor to prevent oxidation. Standard techniques for the purification (removal of oxygen and water vapor) of process gases include (i) the catalytic conversion of oxygen to water vapor and subsequent removal of the water vapor using a molecular sieve, (ii) the use of a gettering furnace usually containing titanium for the removal of both oxygen and water vapor from most inert gases, and (iii) the use of a hot palladium diffusion cell for the removal of impurities from hydrogen. With the first method, the use of corrosive gases and the extent of contamination from sieve materials such as alumina silicates or activated charcoal is questionable. This second method using the titanium gettering furnace is not applicable for the purification of nitrogen and corrosive gases and its capacity for the removal of oxygen or water vapor is somewhat limited. Finally, the hot palladium diffusion cell is applicable to hydrogen only and is susceptible to damage (microcracks in the palladium) if allowed to cool with hydrogen present.

This letter describes the purification of process gases using free aluminum as the primary gettering element in a gallium indium solution at room temperature. The method to be described is simple to integrate in existing semiconductor processing equipment and has the following advantages over the methods mentioned above:

(i) The availability of very high purity gallium, indium, and aluminum eliminates concerning for possible contamination of the process gas from trace impurities in these group III metals. The vapor pressure of these metals at room temperature is sufficiently low to avoid their incorporation in to the process gas being treated.

(ii) By preparing a two-phase solution consisting of the liquid ternary saturated with aluminum and solid aluminum the solution can remain saturated with aluminum as the aluminum is consumed by oxidizing in the presence of the process gas. This allows a very high capacity for the removal of oxygen and water vapor.

(iii) Because of this method of purification is done at room temperature many gases may be treated which would thermally decompose at the moderate temperature used in gettering furnace techniques. Also, a variety of corrosive gases would be applicable providing they do not sufficiently react with Ga, In, and aluminum at room temperature.

Figure 1:
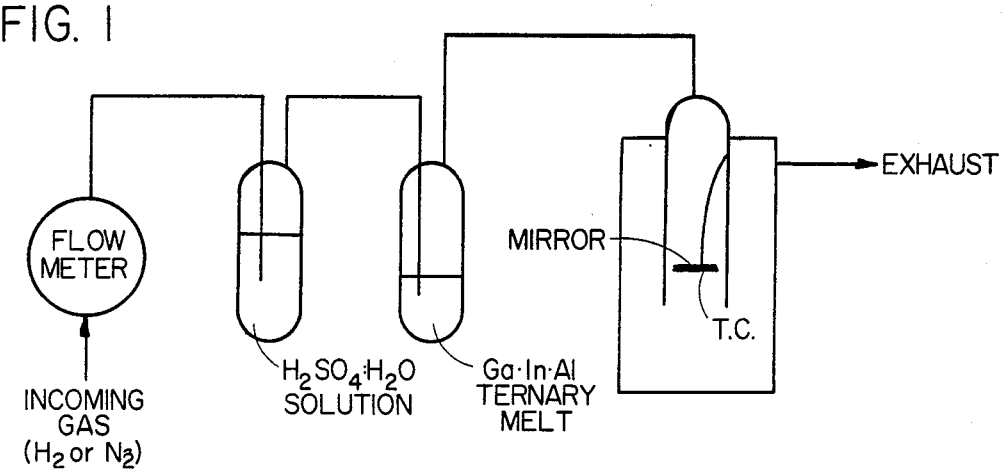
FIG. 1 is a schematic diagram of apparatus to getter $O_2$ and moisture and includes apparatus other than the ternary melt bubbling step, which is associated with the experiment it describes for two gettering gases which are not normally used as reactant gases $H_2$ and $N_2$.

The apparatus used for all experiments reported in the publication Appl. Phys. Lett. 41(1), July 1, 1982 is shown in FIG. 1. The incoming process gas was either hydrogen or nitrogen. The hydrogen was prepared by diffusion through a palladium cell at 300° C. The nitrogen was taken from the "boil off" of a liquid nitrogen source. The flow used in the experiment was fixed at approximately one standard liter per minute.

After passing through a flow meter, the gas was bubbled through an aqueous sulfuric acid solution in order to generate a known partial pressure of water vapor in the incoming gas. This solution contained 78% by volume of sulfuric acid. A total of 5 g of dionized water was present in this solution.

Following the introduction of the water vapor, the gas was bubbled through a ternary melt of gallium, indium, and aluminum. The melt was prepared by first dissolving 10 g of indium into 100 g of gallium at 40° C. This produced a liquid solution at room temperature (24° C.). [M. Hansen, Constitution of Binary Alloys (McGraw-Hill, New York, 1958), 2nd ed., p. 745] Excess aluminum was then added to the gallium indium solution until saturation of aluminum was achieved at room temperature. Approximately 1.8 g of aluminum was dissolved into the liquid melt. The melt was placed in a quartz bubbler which resulted in an equivalent pressure head of 5-mm Hg.

After bubbling through the ternary melt, the gas was passed through a flask designed to measure the dewpoint of moisture in the gas. This flask contains a mirror as shown in FIG. 1, which deflected the incoming gas flow around it. An iron-constantine thermal couple was used to monitor the mirror temperature. The flask was slowly cooled by emersing the flask in liquid nitrogen. The dewpoint was determined by observing the change in the reflectivity of the mirror due to ice condensation from the moisture in the incoming gas. The experimental error for this dewpoint experiment is estimated to be $(+)(-) 5°$ C.

Prior to the use of the aqueous sulfuric acid solution and the gallium-indium-aluminum melt, the dewpoint of the background gas was determined. In addition, the dewpoint melt, the dewpoint of the background gas was determined. In addition, the dewpoint of the gas passing through the aqueous sulfuric acid solution was measured with and without the gallium-indium-aluminum melt.

The use of aluminum as an oxygen gettering element has the primary advantage that is oxide ($Al_2O_3$) is stable and has a low vapor pressure. It has been shown that small amounts of aluminum added to a gallium effusion cell in molecular beam epitaxy has substantially reduced the introduction of gallium oxide into the growth flux. [P. D. Kirchner, J. M. Woodall, J. L. Freeouf, and G. D. Petit, Appl. Phys. Lett. 38, 427 (1981)] However, the use of solid metallic aluminum is not effective for oxygen gettering because its thin protective native oxide prevents further oxidation. The use of the gallium-indium-aluminum ternary melt provides a convenient means for continuously reacting aluminum with oxygen and moisture at room temperature. As the oxygen gettering proceeds the aluminum oxide floats to the top of the melt.

The dewpoint of the starting gases was determined to be approximately $-80°$ C. which corresponds to less than 1 ppm of moisture. Measurements of dewpoints below $-80°$ C. were not attempted because the time required for condensation on the mirror was in excess of several hours. Upon the addition of the aqueous sulfuric acid solution, the gas bubbled through this solution had a dew point of $-20°$ C. This corresponds to 1000 ppm of moisture in the gas which is in fair agreement with vapor pressure data in the literature. [CRC Handbook of Chemistry and Physics (CRC, W. Palm Beach, FL 1977), 58th ed., p. E46.] Passing the gas with 1000 ppm of moisture through a gallium-indium solution had little or no affect on the gases' dewpoint! With the addition of aluminum to the melt, the dewpoint of the gas was initially reduced to below $-80°$ C.

TABLE I

Dewpoint data taken for times after the process gas was treated by the gallium-indium-aluminum melt at room temperature.

| Dewpoint (°C.) | Time (h) |
|---|---|
| −80 | 0 |
| −80 | 1 |
| −80 | 10 |
| −70 | 25 |
| −60 | 40 |
| −45 | 70 |

Table I summarizes dewpoint data taken for times after the gas was introduced through the ternary melt.

As indicated by the table, the melt is slowly becoming saturated with water vapor after approximately 25 h. This is due to the consumption of free aluminum in the melt by oxidation. Small amounts of aluminum oxide on the surfaces of the melt were observed after 1 h and its presence was more pronounced as the experiment proceeded. It appears that approximately 1 g of aluminum in solution with gallium and indium will purify approximately 1500 l of process gas containing 1000 ppm of water vapor.

Figure 4:
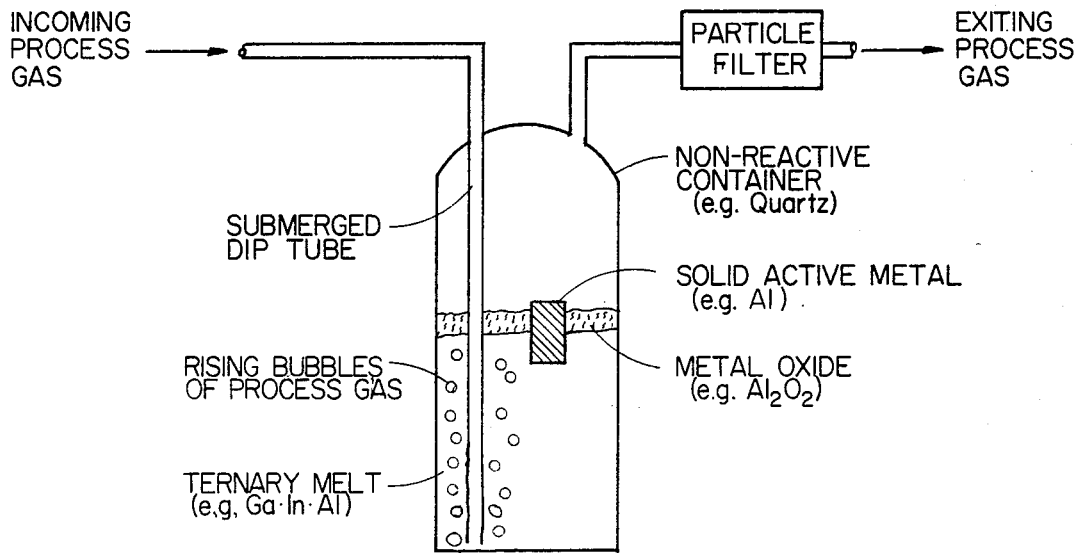
FIG. 4 is a schematic illustration of a getter bubbler constructed in accordance with the teachings of the present invention for use with many reactant gases containing unwanted oxygen, moisture and/or other oxygen bearing gas species in the reactant gas.

Also, we have performed preliminary experiments with two reactant gases: $AsH_3$ and $Ga(CH_4)_3$ commonly used for the chemical vapor deposition of GaAs. We have found that both $AsH_3$ and $Ga(CH_4)_3$ bubbling through the Al—Ga—In melt at room temperature do not decompose; and, thus, it is expected that the melt will getter $O_2$ and $H_2O$ from these reactant gases as well as it does from $H_2$ and $N_2$. All of the components shown in FIG. 1, other than GA—In—Al ternary melt bubbler, are there for experimental purposes only. FIG. 4 shows the range of components necessary to practice the invention of reducing oxygen and moisture in reactant gases.

In conclusion, a relatively simple means for removing oxygen and water vapor from hydrogen and nitrogen was described. Other gases used in processes like chemical vapor deposition (CVD) are likely to be applicable. This would be important since the presence of small amounts of oxygen (as little as 1 ppm) has been shown to be the primary cause for heavy compensation of AlGaAs grown by metal organic CVD. [G. B. Stringfellow, J. Crystal Growth 55, 42(1981).] It should be possible to treat the incoming gases in this process, namely arsine and metal organic vapors diluted in hydrogen, with the gallium-indium-aluminum ternary melt at room temperature resulting in an improvement in the quality of GlGaAs.

As stated in the publication of Appl. Phys. Lett. 42(1), Jan. 1, 1983, the growth of AlGaAs by organometallic vapor phase epitaxy (OMVPE) requires oxygen and moisture-free growth ambients to avoid compensation by an oxygen-related deep luminescence center. [M. J. Tsai, M. M. Tashima, B. L. Twu, and R. L. Moon, presented at the GaAs and Related Compounds Symposium, Albuquerque, NM, September 1982] The major source of moisture appears to have its origin in the arsine source. Methods of gettering previously used to improve the optical film quality include the use of a molecular sieve on the arsine, incorporation of graphite baffles in the reaction cell, [D. W. Kisker and J. N. Miller, Appl. Phys. Lett. 40, 614 (1982)] and the growth of epitaxial buffer layers containing aluminum. [S. D. Hersee, M. A. DiForte-Poisson, M. Baldy, and J. P. Duchemin, J. Cryst. Growth 55, 53 (1981)]

In an earlier letter [J. R. Shealy and J. M. Woodall, Appl. Phys. Lett. 41, 88 (1982)] we reported the use of the Al—Ga—In ternary melt for the removal of large quantities of moisture from hydrogen and nitrogen. Similar results were expected for the purification of arsine, but direct evidence of reducing oxygen and moisture from this gas was not obtained in the previous apparatus. In this letter we report the effects on the low-temperature photoluminescence spectra of $Al_xGa_{1-x}As$ ($x-0.25$) films grown in a low-pressure OMVPE apparatus with the arsine source bubbled through the metallic melt. The results indicate an improvement in the epitaxial layer quality, which demonstrates the effectiveness of this method in gettering moisture and/or oxygen from arsine.

The arsine gas [5N Electronic grade obtained from Phoenix Research, LaMesa, CA.] used in the experiments was taken from a concentrated liquid source. The Al—Ga—In melt was prepared by the procedure described in an earlier publication. [J. R. Shealy and J. M. Woodall, Appl. Phys. Lett. 41, 88 (1982)] Films were grown at 76 Torr with trimethylgallium and trimethylaluminum sources. The substrate temperature and V/III mole ratios used in the experiments were in the range of 700°–800° C. and 20–60, respectively. All films were unintentionally doped.

The film characterization was accomplished using low-temperature (3K) photoluminescence (PL) data. The excitation wavelength and intensity for the PL measurements were 4825 A and 100 mw/cm, [D. W. Kisker and J. N. Miller, Appl. Phys. Lett. 40, 614 (1982)] respectively. The residual acceptors were identified from the PL spectra from the work of Stringfellow and Linnebach [G. B. Stringfellow and R. Linnebach, J. Appl. Phys. 51, 2212 (1980)] and Mircia-Roussel et al., [A. Mircea-Roussel, A. Briere, and J. Hallasi, J. Appl. Phys. 53, 4351 (1982)] and the composition of the AlGaAs was obtained from calibrations obtained by Dingle et al. [R. Dingle, R. A. Logan, and J. R. Arthur, Jr., Inst. Phys. Conf. Ser. 33a, 210 (1977)] The bound exciton transition was identified by observing the relative change of PL intensity with excitation intensity. [G. Wicks, W. I. Wang, C. E. C. Wood, L. F. Eastman, and L. Rathbun, J. Appl. Phys. 52, 5792 (1981)] Additional PL experiments at longer wavelengths produced no observable luminescence due to oxygen-related deep centers. In addition, the background carrier concentration was evaluated using C-V measurements.

Figure 2:
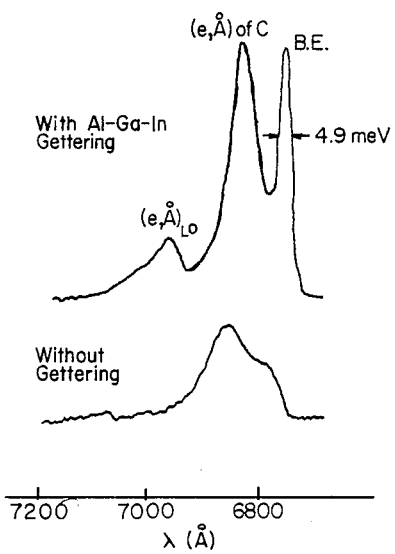
FIG. 2 is a comparison of 3-K PL spectra for Al0.26 Ga0.74As films grown at 700° C. and V/III=40 with and without Al—Ga—In gettering. (The vertical scale is arbitrary and has a shifted zero.
Figure 3:
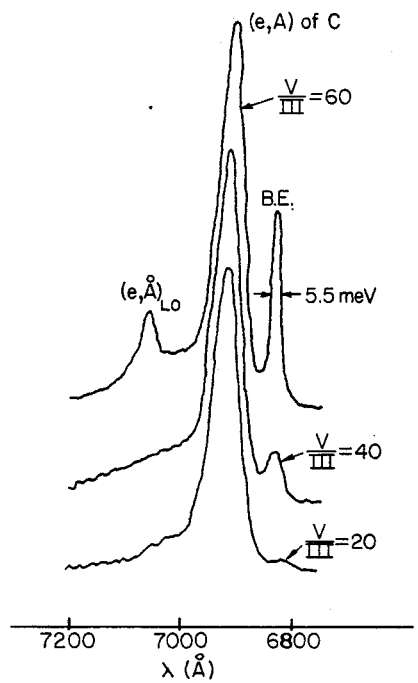
FIG. 3 is a comparison of 3-K PL spectra for Al0.24 Ga0.76As films grown at 800° C. with Al—Ga—In gettering for various V/III ratios. (The vertical scale is arbitrary and has shifted zero).

The effects of treating arsine with the ternary melt are most pronounced at lower growth temperatures. For example, PL spectra are shown in FIG. 2 for $Al_{0.26}Ga_{0.74}As$ layers grown with and without the melt at 700° C. at a V/III ratio of 40. This illustrates that the PL efficiency of the bound exciton (BE) is improved by a factor in excess of 5, and its halfwidth is reduced to less than 5 meV after the use of this gettering technique. The sharpness of this PL spectrum represents an improvement in the state of the art for OMVPE AlGaAs of this alloy composition. The background electron concentration of these films grown at 700° C. was approximately $1 \times 10\text{-}15$ cm$-3$. At higher substrate temperature, e.g., 800° C., the bound exciton PL efficiency is increased slightly by treating the arsine, but this occurs at the expense of greatly increased carbon incorporation in the film. Carbon is the dominant acceptor as seen in FIGS. 2 and 3 for films grown at 700° and 800° C. However, small zinc concentrations were evident when the spectra were taken at higher excitation intensities.

At a given substrate temperature, the bound exciton PL efficiency increases by over an order of magnitude with increased V/III ratio. This is illustrated in FIG. 3 for $Al_{0.24}GA_{0.76}As$ layers grown at 800° C. using the gettering technique. Further improvements in the bound excition structure would be expected if higher V/III ratios could be used. Nevertheless, we find that the best linewidths and PL efficiency of the bound excition are obtained at lower growth temperatures near 700° C. when the gettering technique is used. Not only is carbon incorporation greatly reduced at this temperature, but the net carrier concentration is also lower ($1 \times 10\text{-}15$ cm$-3$). Films grown at 800° C. have electron concentrations of about $5 \times 10\text{-}16$ cm$-3$ when gettering is used. When gettering is not used this value drops to about $1\times 10^{-16}$ cm$^{-3}$, indicating increased compensation by oxygen-related deep centers.

In conclusion, we have demonstrated that by applying a new gettering technique for the removal of oxygen and moisture from the arsine, epitaxial layers of AlGaAs grown by OMVPE have improved the photoluminescence efficiency. The Al—Ga—In melt has a large capacity for the purification of arsine when excess solid aluminum is added to the melt. The best quality AlGaAs films are reproducibly obtained at low growth temperatures ($-700°$ C.) and high V/III ratios when the arsine is treated by this technique.

As described hereinabove, the reactant gas being gettered for oxygen, water vapor and other oxygen bearing gas species has been identified as arsine. Tables 2 and 3 setforth hereinbelow identify many more reactant gases which may, in particular applications, require the gettering of the oxygen water vapor and/or other oxygen gearing gas species. the identity of gases which may be gettered of unwanted oxygen bearing species according to the teachings of the present invention is characterized by those gases which have a slow reaction with gallium-indium and the active gettering metal, i.e. aluminum, and also those which have reactant products which are not volatile. Some of the active gettering metals which might be substituted for aluminum in the ternary melt described hereinabove are magnesium, calcium and lithium. The key factors for selecting the metal for the active ingredient as aforesaid are; they must have a stable low vapor pressure as a metal oxide, also the active metal selected must have a low vapor pressure at the operating temperature herein described as a moderate range of temperatures, increasing from room temperature to avoid their incorporation in the process gas (reactant gas). Finally, the active metal must have a slow reaction with the process gas (reactant gas). FIG. 15.5 on page 116 and related text of a text book by R. A. Thermodynamics of solids (Wiley, New York 1972) 2nd ed., should be consulted in selecting the active metal ingredient with the qualities aforesaid.

When reactants HCL (Hydrogen Chloride) and $(C_2H_5)_3Ga$ were gettered in accordance with the present invention there was no observable exothermic reaction, or no observable reaction products.

The present invention operates to getter oxygen and moisture from the process gas (reactant gas) to a high degree of purity. However, while it accomplishes that function, it also getters the oxygen from other oxygen bearing gas species such as $CO_2$ and $NO_2$.

METAL BUBBLER

A schematic representation of a non-batchprocess for the metallic bubbler is given in FIG. 4. This flow through system consists of a non-reactant container (e.g. quartz) in the form of a bubbler with a dip tube submerged in the liquid metal as shown. The oncoming process gas forms bubbles in the liquid metal as it exits the dip tube. A sufficient height of the ternary melt is placed in the bubbler such that the transit time of the gas bubble to the top of the melt is long enough to allow the oxygen, moisture or other oxygen bearing gas to diffuse to the bubbles outer edge to come in contact with the active gettering metal (e.g. Al). The height of the solution in the bubbler is adjusted according to the flow rate, and oxygen concentration in the incoming process gas. As the Al (or other active ingredient) in solution with the Ga—In oxidizes, the solid metal oxide ($Al_2O_3$) floats to the top of the melt which decreases the amount of Al in solution. This event causes the melt to become undersaturated with aluminum (or other active metal), hence more Al from the solid metal dissolves into the ternary melt. The shape of the solid aluminum is arbitrary and there is no limit (other than the bubbler size) to the amount of solid aluminum which can be added to this system. This allows extremely large quantities of oxygen, water vapor, etc. to be removed from the process gas without disturbing the flow of gas through the system. The gallium and indium in the melt in FIG. 4 is twenty percent indium by weight, twice the ratio as described to be in FIG. 1 on the gallium rich side of the eutectic. If large concentrations of the gettered species are present in the process gas, the getter reaction rate is increased by increasing the indium concentration in the melt which allows more aluminum to go in to solution at a given temperature.

Other melt compositions and operating temperatures as deduced from the Ga—In eutectic phase diagram are covered by this invention for example, for the following operating temperatures of 16.5° C. (eutectic) 20° C., 30° C., and 60° C. the corresponding range of melt composition which would remain liquid and thus applicable to the invention are 24.5%, 12–27%, 0–30% and 0–52%. It is assumed the presence of aluminum (or the other active gettering metal) in the melt does not appreciably affect the phase diagram. Operating temperatures above melting 30° C. melting of gallium would allow a binary Ga—Al melt to be used for gettering.

The piece of aluminum protrudes into the melt based on the bouyancy and thus is continuously moving down ward as the aluminum in the piece (rod or bar, etc.) goes into solution over time as aluminum oxide is formed from the solution. The length of the piece is a matter of choice.

EPITAXIAL GROWTH PROCESSES OF SEMICONDUCTOR

The application of this invention is illustrated schematically to a general epitaxical growth process in FIG. 5. As shown three lines containing a process gas labled source gas, dopant gas and HCl are connected to a bubbler containing the metal ternary melt and then to the epitaxical reactor. The HCl line is used for in situ etching the host substrate material prior to growth; and dopant gases are typically diluted in hydrogen and are used for introducing a controlled concentration of impurities in the epitaxical layer and the source gas contains the species which provides the major component or components of the epitaxical film. Examples of these gases for the particular cases of silicon vapor phase epitacy, GaAs and related components hydride or halide vapor phase epitaxy and organometallic vapor phase epitaxy are given in Tables 2A, 2B and 2C, respectively.

TABLE 2A

| EPITAXIAL GROWTH PROCESS SILICON VAPOR PHASE EPITAXY (VPE) ||
|---|---|
| COMMON SOURCE GASES | COMMON DOPANT GASES |
| (1) $SiCl_4$ | (1) $PH_3$ |
| (2) $SiHCl_3$ | (2) $B_2H_6$ |
| (3) $SiH_2Cl_2$ | |
| (4) $SiH_3Cl$ | |
| (5) $SiH_4$ | |

TABLE 2B

(GaAs AND RELATED COMPOUNDS) HYDRIDE OR HALIDE VPE

| COMMON SOURCE GASES | COMMON DOPANTS |
|---|---|
| (1) $AsH_3$ | (1) $H_2S$ |
| (2) $PH_3$ | (2) $H_2Se$ |
| (3) $AsCl_3$ | (3) $SnCl_4$ |
| (4) $PCl_3$ | |

TABLE 2C

(COMPOUND SEMICONDUCTORS) ORGANOMETALLIC VAPOR PHASE EPITAXY (OMVPE)

COMMON SOURCE GASES (TYPICALLY IN $H_2$ CARRIER)

(1) ORGANOMETALLICS
- (a) ETHYL GROUP
  - $(C_2H_5)_2Te$
  - $(C_2H_5)_2Zn$
  - $(C_2H_5)_3Ga$
  - $(C_2H_5)_3Al$
  - $(C_2H_5)_3In$
  - $(C_2H_5)_4Pb$
- (b) METHYL GROUP
  - $(CH_3)_2Zn$, $(CH_3)_3As$
  - $(CH_3)_2Cd$, $(CH_3)_3Sb$
  - $(CH_3)_2Te$, $(CH_3)_3Bi$
  - $(CH_3)_3Ga$, $(CH_3)_4Ge$
  - $(CH_3)_3Al$, $(CH_3)_4Sn$
  - $(CH_3)_3In$ (2) HYDRIDES
- $AsH_3$
- $PH_3$
- $SbH_3$
- $NH_3$

COMMON DOPANT GASES

| | |
|---|---|
| (1) $CH_4$ | (4) $H_2S$ |
| (2) $SiH_4$ | (5) $H_2Se$ |
| (3) $GeH_4$ | (6) $H_2Te$ |

It is interesting to note that in each of these processes moisture present in the growth ambient at levels typically greater than several parts per million results in electronically active defects in the epitaxial grown layers. This invention is applicable to all the gases and liquids suspended in a carrier gas (such as $AsCl_3$ or most organometallics) and will improve these semiconductors quality and ultimately an electronic device's performance built on these materials. In general, these epitaxical processs are in a subclass of Chemical Vapor Deposition (CVD) processes where amorphous thin films are deposited and are not epitaxial. Because this invention is applicable to the majority of reactant gases used in CVD process, including plasma enhanced chemical vapor deposition techniques, this invention covers the use of the metal melt bubbler for removing unwanted oxygen water and vapor and other oxygen bearing species from reactant source gas used in all chemical vapor deposition processes.

PLASMA ETCHING PROCESSES

The application of this invention to the gases used in plasma etching processes is illustrated schematically in FIG. 6. Also shown in the figure is an oxygen line which in connected to the plasma reactor through a valve. In many cases oxygen is mixed with an etchant gas to change the etch rate or etch properties. For example, if oxygen is added to CF when etching single crystal silicon, the eteh is isotropic. In some cases anisotropic etching behavior is needed in silicon device processing. This requires a moisture and oxygen free ambient in the plasma reactor for the best result. Hence, by passing the etchant gas, in this case $CF_4$, through the metal bubbler described in this invention improved anisotropic etching of silicon is realized.

Plasma etching processes have been developed for a variety of metals, silicides, and semiconductors where oxygen and moisture free ambients are desirable. A list of the etchant gases used for a number of common plasma etch processes is given in Table 3.

TABLE 3

ETCHANT GAS

PLASMA ETCHING OF METALS

| METAL | |
|---|---|
| Au | $CClF_3$, $C_2Cl_2F_4$ |
| Cr | $CCl_2$, $CCl_4$ |
| Mo | $CF_4$, $CF_3Br$, $CCl_2F_2$, $C_2Cl_3F_3$ |
| V | $C_2F_6$ |
| W | $CF_4$, $CHF_3$ |

PLASMA ETCHING OF SILICIDES

| SILICIDE | |
|---|---|
| $MoSi_2$ | $SF_6$ |

PLASMA ETCHING OF SEMICONDUCTORS

| SEMICONDUCTOR | |
|---|---|
| Si | $CF_4$, $CHF_3$, $CF_3Cl$, $Cf_3Br$, $Cl_2$ |
| GaAs | $Cl_2$, HCL, $BCl_3$, $CCl_2F_2$, $CCl_4$, $PCl_3$ |
| InP | $Cl_2$, $CCl_4$ |
| GaSb | $Cl_2$ |

This invention is applicable to all of these reactant gases as well as other process gases in the category described above.

Hydrogen chloride gas is used in a broad range of industrial processes. It is typically handled with stainless steel containers and tubing to transport the gas to the process. However, when moisture is present in small quantities (a few ppm) in the HCl gas, a significant amount of corrosion takes place on the stainless steel as the HCl moisture reach it. Hence, by removing the residual moisture in the HCl gas at the source using this invention, a cleaner (freer form contaminates from the corroded stainless steel) more reliable process results.

Accordingly, it is to be understood that the embodiments of the invention herein described are merely illustrative of the application of the principles of the invention. Reference herein to details of the illustrated embodiment is not intended to limit the scope of the claims which themselves recite those features regarded as essential to the invention.

I claim:

1. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and calcium as an active gettering metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from the calcium component of the melt is incorporated in the reactant gas being processed, whereby oxygen in the gas reacts with the calcium to form calcium oxides and the degree of purification depends on the completion of the oxidation of the calcium being within the time required for the oxygen bearing species in the reactant gas to reach the bubbles outer edge where the reaction with the calcium occurs, the time required being directly dependent on the height of the ternary melt relative to the size of the bubble;

b. maintaining a quantity of the calcium in the ternary melt in solid form, so that theternary melt remains saturated with the calcium, whereby the calcium removed from the ternary melt in the form of oxides is replaced from the solid calcium.

2. A method of treating reactant gases by removing oxygen and water vapor and other oxygen bearing gas species, including trace amounts thereof, comprising the steps of:

a. in a nonreactive container containing a liquid solution comprising a ternary melt of gallium-indium and calcium as an active gettering metal in liquid phase, bubbling the reactant gas through a liquid solution at a operating temperature in the range from 16.5° C., up to a temperature below that at which the gas being treated would thermally decompose or a significant amount of vapor from the calcium component of the melt is incorporated in the reactant gas being processed, whereby oxygen in the gas reacts with the calcium to form calcium oxides;

b. maintaining a quantity of the calcium in the ternary melt in solid form, so that the ternary melt remains saturated with the calcium, whereby the calcium removed from the ternary melt in the form of oxides is replaced from the solid calcium.

3. The method set forth in claim 2, wherein the ratio of said gallium and indium in said melt being maintained in a range centered on the gallium side of the eutectic for gallium-indium, such that the melt will stay in a liquid phase over a wider and lower range of operating temperature variations during the gettering process, the height of ternary melt through which the bubbles pass being increased to accomodate, to increase flows of reactant gases to be gettered or increased amounts of oxygen and water vapor and other oxygen bearing gas species in the reactant gases.

4. A method of treating reactant gases by removing oxygen and water vapor and other oxygen bearing gas species, including trace amounts thereof, comprising the steps of:

a. in a nonreactive container containing a liquid solution comprising a ternary melt of gallium-indium and lithium as an active gettering metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from the lithium component of the melt is incorporated in the reactant gas being processed, whereby oxygen in the gas reacts with the lithium to form lithium oxides and the degree of purification depends on the completion of the oxidation of the lithium being within the time required for the oxygen bearing species in the reactant gas to reach the bubbles outer edge where the reaction with the lithium occurs, the time required being directly dependent on the height of the ternary melt relative to the size of the bubble;

b. maintaining a quantity of the lithium in the ternary melt in solid form, so that the ternary melt remains saturated with the lithium, whereby the lithium removed from the ternary melt in the form of oxides is replaced from the solid lithium.

5. A method of treating reactant gases by removing oxygen and water vapor and other oxygen bearing gas species, including trace amounts thereof, comprising the steps of:

a. in a nonreactive container containing a liquid solution comprising a ternary melt of gallium-indium and lithium as an active gettering metal in liquid phase, bubbling the reactant gas through a liquid solution at a operating temperature in the range from 16.5° C., up to a temperature below that at which the gas being treated would thermally decompose or a significant amount of vapor from the lithium component of the melt is incorporated in the reactant gas being processed, whereby oxygen in the gas reacts with the lithium to form lithium oxides;

b. maintaining a quantity of the lithium in the ternary melt in solid form, so that the ternary melt remains saturated with the lithium, whereby the lithium removed from the ternary melt in the form of oxides is replaced from the solid lithium.

6. The method set forth in claim 5, wherein the ratio of said gallium and indium in said melt being maintained in a range centered on the gallium side of the eutectic for gallium-indium, such that the melt will stay in a liquid phase over a wider and lower range of operating temperature variations during the gettering process, the height of ternary melt through which the bubbles pass being increased to accomodate, to increase flows of reactant gases to be gettered or increased amounts of oxygen and water vapor and other oxygen bearing gas species in the reactant gas.

7. A method of treating reactant gases by removing oxygen and water vapor and other oxygen bearing gas species, including trace amounts thereof, comprising the steps of:

a. in a nonreactive container containing a liquid solution comprising a ternary melt of gallium-indium and an active gettering metal selected from the group of aluminum, magnesium, calcium and lithium in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the active gettering metal to form metal oxides and the degree of purification depends on the completion of the oxidation of the active gettering metal being within the time required for the oxygen bearing species in the reactant gas to reach the bubbles outer edge where the reaction with the active gettering metal occurs, the time required being directly dependent on the height of the ternary melt relative to the size of the bubble;

b. maintaining a quantity of the selected active gettering metal in the ternary melt in solid form, so that the ternary melt remains saturated with the active gettering metal, whereby the active gettering metal removed from the ternary melt in the form of oxides is replaced from the solid metal;

c. maintaining the ratio of said gallium and indium in said melt being maintained in a range centered on the gallium rich side of the eutectic for gallium-indium, such that the melt will stay in a liquid phase over a wider and lower range of operating temperature variations during the gettering process, and the height of ternary melt through through which the bubbles pass being increased to accomodate, to increase flows of reactant gases to be gettered or increased amounts of oxygen and water vapor and other oxygen bearing gas species in the reactant gas.

8. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and aluminum as an active gettering metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the aluminum to form aluminum oxides and the degree of purification depends on the completion of the oxidation of the aluminum being within the time required for the oxygen bearing species in the reactant gas to reach the bubbles outer edge where the reaction with the aluminum occurs, the time required being directly dependent on the height of the ternary melt relative to the size of the bubble;
   b. maintaining a quantity of the aluminum in the ternary melt in solid form, so that the ternary melt remains saturated with the aluminum, whereby the aluminum removed from the ternary melt in the form of oxides is replaced from the solid aluminum;
   c. maintaining the ratio of said gallium and indium in said melt being maintained in a range centered on the gallium side of the eutectic for gallium-indium, such that the melt will stay in a liquid phase over a wider and lower range of operating temperature variations during the gettering process, and the height of ternary melt through which the bubbles pass being increased to accomodate, to increase flows of reactant gases to be gettered or increased amounts of oxygen and water vapor and other oxygen bearing gas species in the reactant gas.

9. The method set forth in claim 8 wherein the reactant gases from which oxygen, water vapor, and other oxygen bearing species are removed including trace amounts thereof as arsine gases.

10. The method set forth in claim 8 wherein the reactant gases from which oxygen, water vapor, and other oxygen bearing species are removed including trace amounts thereof are hydrogen chloride gases.

11. The method set forth in claim 8 wherein the reactant gases from which oxygen, water vapor, and other oxygen bearing species including trace amounts thereof are trimethylgallium gases.

12. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and magnesium as an active gettering metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the magnesium to form magnesium oxides and the degree of purification depends on the completion of the oxidation of the magnesium being within the time required for the oxygen bearing species in the reactant gas to reach the bubbles outer edge where the reaction with the magnesium occurs, the time required being directly dependent on the height of the ternary melt relative to the size of the bubble;
   b. maintaining a quantity of the magnesium in the ternary melt in solid form, so that the ternary melt remains saturated with the magnesium, whereby the magnesium removed from the ternary melt in the form of oxides is replaced from the solid magnesium;
   c. maintaining the ratio of said gallium and indium in said melt being maintained in a range centered on the gallium side of the eutectic for gallium-indium, such that the melt will stay in a liquid phase over a wider and lower range of operating temperature variations during the gettering process, the height of ternary melt through which the bubbles pass being increased to accomodate, to increase flows of reactant gases to be gettered or increased amounts of oxygen and water vapor and other oxygen bearing gas species in the reactant gas.

13. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and an active gettering metal selected from the group of aluminum, magnesium, calcium and lithium in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the active gettering metal to form metal oxides;
   b. during the bubbling step, the transit time of the gas bubble to the top of the melt being long enough to allow the oxygen, moisture or other oxygen bearing gas to diffuse to the bubbles outer edge to come in contact with the active gettering metal in solution such as to provide sufficient oxidation of the active gettering metal to result in a high purity reactant gas containing less than one part per million of oxygen bearing species;
   c. maintaining a quantity of the selected active gettering metal in the ternary melt in solid form, so that the ternary melt remains saturated with the active gettering metal, whereby the active gettering metal removed from the ternary melt in the form of oxides is replaced from the solid metal.

14. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and aluminum as getter metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the aluminum to form aluminum oxides;
   b. during the bubbling step, the transit time of the gas bubble to the top of the melt being long enough to allow the oxygen, moisture or other oxygen bearing gas to diffuse to the bubbles outer edge to come in contact with the aluminum in solution such as to provide sufficient oxidation of the aluminum to result in a high purity reactant gas containing less than one part per million of oxygen bearing species;
   c. maintaining a quantity of the aluminum in the ternary melt in solid form, so that the ternary meld remains saturated with the aluminum, whereby the aluminum removed from the ternary melt in the form of oxides is replaced from the solid aluminum.

15. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and magnesium as getter metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the magnesium to form magnesium oxides;
   b. during bubbling step, the transit time of the gas bubble to the top of the melt being long enough to allow the oxygen, moisture or other oxygen bearing gas to diffuse to the bubbles outer edge to come in contact with the magnesium in solution such as to provide sufficient oxidation of the magnesium to result in a high purity reactant gas containing less than one part per million of oxygen bearing species;
   c. maintaining a quantity of the magnesium in the ternary melt in solid form, so that the ternary meld remains saturated with the magnesium, whereby the magnesium removed from the ternary melt in the form of oxides is replaced from the solid magnesium.

16. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and lithium as getter metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the lithium to form lithium oxides;
   b. during the bubbling step, the transit time of the gas bubble to the top of the melt being long enough to allow the oxygen, moisture or other oxygen bearing gas to diffuse to the bubbles outer edge to come in contact with the lithium in solution such as to provide sufficient oxidation of the lithium to result in a high purity reactant gas containing less than one part per million of oxygen bearing species;
   c. maintaining a quantity of the lithium in the ternary melt in solid form, so that the ternary meld remains saturated with the lithium, whereby the lithium removed from the ternary melt in the form of oxides is replaced from the solid lithium.

17. A method of treating reactant gases by removing oxygen and water vapor and other oxygen bearing gas species, including trace amounts thereof, comprising the steps of:
   a. in a nonreactive container containing a liquid solution comprising a ternary melt of gallium-indium and calcium as getter metal in liquid phase, bubbling the reactant gas through a liquid solution at a operating temperature in the range from a low room temperature at least high enough that the solution remains liquid, up to a temperature below that at which the gas being treated would thermally decompose or a significant amount of vapor from any component of the melt is incorporated in the reactant gas being processed, whereby oxygen in the gas reacts with the calcium to form calcium oxides;
   b. during the bubbling step, the transit time of the gas bubble to the top of the melt being long enough to allow the oxygen, moisture or other oxygen bearing gas to diffuse to the bubbles outer edge to come in contact with the calcium in solution such as to provide sufficient oxidation of the calcium to result in a high purity reactant gas containing less than one part per million of oxygen bearing species;
   c. maintaining a quantity of the calcium in the ternary melt in solid form, so that the ternary meld remains saturated with the calcium, whereby the calcium removed from the ternary melt in the form of oxides is replaced from the solid calcium.

* * * * *